United States Patent [19]
Tabibi et al.

[11] Patent Number: 5,672,358
[45] Date of Patent: Sep. 30, 1997

[54] CONTROLLED RELEASE AQUEOUS EMULSION

[75] Inventors: S. Esmail Tabibi, Rockville, Md.; Robert W. Mendes, Dedham, Mass.; Nitin P. Pathak, Clearwater, Fla.

[73] Assignee: Ascent Pharmaceuticals, Inc., Billerica, Mass.

[21] Appl. No.: 491,626

[22] Filed: Jun. 19, 1995

Related U.S. Application Data

[63] Continuation-in-part of Ser. No. 263,277, Jun. 21, 1994, abandoned.
[51] Int. Cl.⁶ .......................... A61K 9/107; A61K 9/127
[52] U.S. Cl. .......................... 424/450; 424/484; 424/502
[58] Field of Search .......................... 424/484, 502, 424/450

[56] References Cited

U.S. PATENT DOCUMENTS

| | | |
|---|---|---|
| 4,952,402 | 8/1990 | Sparks et al. . |
| 5,188,837 | 2/1993 | Domb . |
| 5,444,041 | 8/1995 | Owen et al. . |

FOREIGN PATENT DOCUMENTS

WO93/02665  2/1993  WIPO .

OTHER PUBLICATIONS

Domb, *Proceed, Intern. Symp. Control. Rel. Bioact. Mat.*, 20:121–122 (Jul. 1993).
*The Lecithin Book*, Central Soya, Chemurgy Division, Forth Wayne, IN (1993).
PCT/US95/07908 International Search Report.

*Primary Examiner*—Jeffrey C. Mullis
*Attorney, Agent, or Firm*—Welsh & Katz, Ltd.

[57] ABSTRACT

A controlled release aqueous emulsion is disclosed, as are its method of manufacture and use as a vehicle for delivering medicaments in liquid form. A contemplated emulsion comprises an oil-in-water emulsion having an average oil particle size of about 100 nm to about 250 nm, a pH value of about 4.5 to about 8.0 and a viscosity at 20°–25° C. of 1 to about 1000 cps. The water phase constitutes at least 25 weight percent of the total composition. The oil phase is a wax matrix that is a wax having a melting point of about 40° to about 80° C. and is present in an amount of about 3 to about 30 percent of the total composition. A pharmaceutically effective amount of a pharmacologically active compound that is free from decomposition at a temperature below about 90° C. is dissolved or dispersed in the wax matrix. The oil and water phases are emulsified by an emulsifying agent that provides freedom from phase separation at a pH value of about 4.5 to about 8, while also providing phase separation at a pH value below about 2.0. The emulsifier, based on lecithin, is present at about 2 to about 20 weight percent of the total composition. The composition can also contain zero to about 35 weight percent additional excipient.

23 Claims, 4 Drawing Sheets

CONTROLLED RELEASE AQUEOUS EMULSION

CROSS REFERENCE TO RELATED APPLICATION

This is a continuation in part of application Ser. No. 08/263,277, filed Jun. 21, 1994, now abandoned whose disclosure is herein incorporated by reference.

DESCRIPTION

1. Technical Field

The present invention relates to the controlled release of a pharmacologically active compound, and more particularly to an aqueous controlled release composition that is a pourable liquid.

2. Background Art

Controlled release of pharmacologically active compounds, medicaments or drugs is a well known phenomenon. Substantially all of such formulations are solids in tablet or capsule form. As such, those compositions can be difficult for children and even adults to swallow.

In some solid formulations, individual medicament particles are encased in a coating of varying thickness. The different coating thicknesses take different times to dissolve during passage of the particles through the gastrointestinal (GI) tract, thereby providing controlled release of the medicament.

Controlled release microparticles said to be dispersible in aqueous media for oral ingestion are disclosed in U.S. Pat. No. 4,952,402. In accordance with that patent, a polymer-coating solution is formed in a solvent for the polymer. The pharmacologically active agent is dissolved or dispersed in the polymer solution. The resulting solution is then dried to form micro-particles referred to as pharmasomes having an average size of 0.1 to 125 µm in which the pharmacologically active agent is uniformly distributed throughout the polymeric materials, as compared to being encapsulated by the polymer.

The pharmasomes of U.S. Pat. No. 4,952,402 are said to be capable of formulation in solid form as a dusting powder, filled in capsules as well as in tablet form or in suppositories. The pharmasomes are also said to be capable of formulation in creams and ointments for topical applications. Oral suspensions and syrups containing the pharmasomes are also disclosed.

The disclosed suspensions and syrups, while containing some water, are substantially non-aqueous. For example, a settling dispersion of a guaiphenesin-containing pharmasome in 70 weight percent sorbitol was reported, as was a syrup made from a theophylline-containing pharmasome in 66 weight percent sugar solution in water. Another theophylline-containing pharmasome suspension was described in a vehicle containing 89.9 weight percent of a 70 weight percent sorbitol solution, 10 weight percent glycerin and 0.1 weight percent polysorbate-80. A similar suspension was also reported using an acetaminophen-containing pharmasome.

Another known system said to be useful in aqueous liquid form utilized an ionically charged medicament bound to an ion exchange resin particle; the medicament/resin being coated within a membrane. Here, the medicament remains bound to the resin in aqueous environments so long as the environment is relatively free of other ionic species. Once ingested, the ions present in the GI tract are sorbed through the membrane and displace the medicament. Release rate in this system is typically controlled by the porosity and thickness of the membrane coating.

One commercial embodiment of the above technology is believed to be the material sold under the trademark TUSSIONEX® by Fisons Corporation of Rochester, N.Y. The product contains protonated hydrocodone and protonated chlorpheniramine, each of which is complexed to sulfonated styrene-divinylbenzene copolymer particles that are individually coated with an ethylcellulose membrane. The resulting particles are settleably suspended in a vehicle that contains high fructose corn syrup, polyethylene glycol 3350, polysorbate 80, propylene glycol, purified water, sucrose and xanthan gum. Another commercially available product sold under the trademark DELSYM® contains a complex of dextromethorphan complexed to the resin a similar vehicle.

International application WO 93/02665 published Feb. 18, 1993 describes water-in-oil microemulsions having controlled release properties. Those emulsions are said to form spontaneously on mixing and contain a lipophilic phase having a long chain fatty acid triglyceride and a low HLB surfactant, a high HLB surfactant, an aqueous hydrophilic phase and a water-soluble therapeutic agent. The disclosed microemulsions are said to be useful for topical administration of the therapeutic agent, or for oral administration when loaded within soft gelatin capsules.

Domb, Proceed. Intern. Symp. Control. Rel. Bioact. Mat., 20:121–122 (1993) described a so-called Liposphere™ injectable delivery system. That system had solid triglyceride that solidified at a temperature below 30° C. dispersed with a phospholipid in an aqueous solution that was injected into the recipient. The particles contained a drug and had an average size of about 1–20 µm. That system was said to provide prolonged release oxytetracycline upon intramuscular injection into rats.

Prolonged release has also been achieved using injections of drug-containing liposomes, as compared to a peroral route of administration. Liposomes contain a bilayer membrane that is typically composed of phospholipid molecules. The bilayer surrounds an aqueous core that can contain a water-soluble drug, or a lipid-soluble drug can be imbedded in the lipid bilayer. In most cases, efflux of a water-soluble drug from the interior aqueous space is quite limited. Liposomes typically vary in size from 0.02 µm to 20 µm. The use of liposomes containing 1-D-arabinofuranosyl cytosine to treat a mouse leukemia is discussed in Mayhew et al., Cancer Treatment Rep., 83(11–12):1923–1928 (1979), and the citations therein.

It would be of interest to the pharmaceutical industry and the public, particularly those members of the public that have difficulty swallowing tablets and capsules, if a non-settling aqueous controlled release drug composition were available. The disclosure that follows describes one such composition.

BRIEF SUMMARY OF THE INVENTION

The present invention contemplates a drinkable aqueous emulsion that provides controlled release of a pharmacologically active compound, a drug or medicament, and processes for administering and preparing the same.

Thus, a controlled release liquid pharmaceutical composition is contemplated that includes a water phase and an oil phase. The composition is an oil-in-water emulsion having an average oil phase particle size of about 100 to about 250 nm, a pH value of about 4.5 to about 8.0 and a viscosity at 20°–25° C. of 1 to about 1000 cps. The aqueous phase constitutes at least 25 and preferably at least 50 weight percent of the total composition. The oil phase comprises a wax matrix having a melting point of about 40° to about 80° C. and is present in an amount of about 3 to about 30 percent of the total composition. An effective amount of a pharmacologically active compound that is free from decomposition at a temperature below about 90° C. is dissolved or dispersed in the wax matrix. The oil and aqueous phases are emulsified by an emulsifying agent that provides freedom from phase separation at a pH value of about 4.5 to about 8, while also providing phase separation or breaking of the emulsion at a pH value below about 2.0. The composition contains zero to about 35 weight percent additional excipient such as sweetener, flavorant, preservative and the like.

A preferred wax matrix is an ester formed from a $C_{14}$–$C_{22}$ monohydric alcohol and a $C_{14}$–$C_{22}$ monocarboxylic acid or a natural wax. More preferably, the wax matrix is present in an amount of about 5 to about 20 weight percent of the total composition, and has a melting point of about 45° to about 70°. A particularly preferred wax matrix is beeswax. A more particularly preferred wax matrix is cetearyl behenate sold by Koster Keunan, Inc. under the trademark Kester™ 62. A particularly preferred phospholipid emulsifier is a vegetable lecithin further containing ethoxylated mono-diglycerides and propylene glycol; (i.e., an admixture of lecithin, ethoxylated mono-diglycerides and propylene glycol) having an HLB number of 12.

An above-described aqueous liquid controlled release pharmaceutical composition emulsion is administered to a mammalian patient to provide controlled release of the medicament by providing such a composition to a recipient in need of the medicament, and per orally administering the liquid composition to the recipient.

A process for preparing a controlled release oil-in-water pharmaceutical composition is also contemplated. That process comprises the steps of:

(a) providing a homogeneous molten admixture at a temperature below about 85° C. The molten admixture contains (i) a wax matrix having dissolved or dispersed therein (ii) a pharmaceutically effective amount of a pharmacologically active compound and (iii) an emulsifier. The contemplated wax matrix is a wax having a melting point of about 40° to about 80° C. The ratio of wax matrix to emulsifier is about 1:1 to about 5:1, and preferably about 3:2 to about 5:1. The pharmacologically active compound utilized is free from decomposition below about 90° C.

(b) A water phase is provided having a temperature about 5° C. higher than that of the molten admixture.

(c) The molten admixture as oil phase is microemulsified with a sufficient amount of the water phase at the temperature of the water phase to form non-settling emulsion having a particle size of about 100 to about 250 nm in which the aqueous phase is external.

(d) The resultant emulsion is then cooled to a temperature of about 10° to about 25° C. (ambient room temperature).

(e) Zero to about 35 percent additional excipient and sufficient water are admixed, and the pH value is adjusted, if necessary, such that the formed pharmaceutical composition has a viscosity at 20°–25° C. of about 1 to about 1000 cps, a pH value of about 4.5 to about 8.0, a water phase that constitutes at least 25 weight percent of the total composition, and an oil phase that contains (i) the wax matrix constituting about 3 to about 30 weight percent of the total composition, (ii) the emulsifier constituting about 2 to about 20 weight percent of the total composition, and (iii) an effective amount of the pharmacologically active compound.

BRIEF DESCRIPTION OF THE DRAWINGS

In the drawings forming a part of this disclosure.

The present invention has several benefits and advantages.

One benefit of the invention is a drinkable controlled release medicament composition that can readily be administered to children and adults that have difficulty in swallowing tablets, capsules or other solid medicament forms.

Another benefit of the invention is that a contemplated composition is relatively easy and inexpensive to prepare.

An advantage of the invention is that there is little if any bleeding of the medicament from the oil phase to the aqueous phase of the emulsion on storage.

Still further benefits and advantages of the invention will be apparent to the skilled worker from the description that follows.

DETAILED DESCRIPTION OF THE INVENTION

The present invention contemplates a pourable aqueous controlled release emulsion composition of a pharmacologically active compound (medicament or drug). A process for preparing such a composition is also contemplated.

A. Composition

A controlled release pharmaceutical composition is contemplated that includes a water phase and an oil phase. The composition is a non-settling (stable) oil-in-water emulsion having an average oil phase particle size of about 100 to about 250 nm, a pH value of about 4.5 to about 8.0 and a viscosity at 20°–25° C. of 1 to about 1000 cps so that the composition is liquid at usually used temperatures of administration. The aqueous phase constitutes at least 25 weight percent of the total composition. The oil phase comprises a wax matrix having a melting point of about 40° to about 80° C. and is present in an amount of about 3 to about 30 percent of the total composition. An effective amount of a pharmacologically active compound that is free from decomposition at a temperature below about 90° C. is dissolved in the wax matrix. The oil and water phases are emulsified by an emulsifier that provides freedom from phase separation at the pH value of the composition, e.g., about 4.5 to about 8.0, while also permitting the emulsion to break to form separate oil and aqueous phases at a pH value below about 2.0. The composition contains zero to about 35 weight percent additional excipient; i.e., inactive ingredients other than the emulsifier, oil and aqueous phases.

A contemplated liquid emulsion thus contains two immiscible phases, which, according to usual terminology are referred to as the water (aqueous) and oil phases. It is to be understood from the use of those terms that the water or aqueous phase can contain water as well as ingredients such as sweeteners, flavorants, buffer salts, preservatives and co-solvents such as propylene glycol or glycerin and other water-soluble ingredients (additional excipients), whereas the oil phase need not contain an oil, per se, but rather contains hydrophobic, oleaginous substances that are immiscible in water.

Being an oil-in-water (o/w) emulsion, the water phase is the external phase and the oil phase is the internal phase. Addition of water to a contemplated emulsion merely causes dilution as is the case when milk is diluted with water. Water of the water (aqueous) phase constitutes at least about 25 and more preferably at least 50 weight percent of the entire emulsion composition. The aqueous phase more preferably constitutes at least about 60 weight percent and most preferably about 70 weight percent of the total composition.

A contemplated emulsion is also non-settling or separating as is homogenized milk. Thus, the emulsion does not separate into its aqueous and oil phases on standing when stored at a temperature of about 20° C. to about 30° C. over a period of one year at the pH value of the composition. As a consequence of the emulsion being non-settling, the emulsion is homogeneous and need not be reshaken prior to use, although shaking has no ill effects upon the composition, and is preferred following usual practice. The emulsified particles of the oil phase have an average size of about 100 to about 250 nm, and more preferably about 150 nm to about 200 nm.

The emulsion composition has a pH value of about 4.5 to about 8.0, and more preferably about 5.5 to about 7.5, and is free from settling or separation at those pH values. Those pH values can be achieved by use of well known pharmacologically acceptable buffering materials, but is more preferably a result of admixture of the ingredients used, plus a typically minor adjustment with a pharmaceutically acceptable acid such as hydrochloric, sulfuric, phosphoric or acetic acids or base such as sodium or potassium hydroxide, or both to achieve a desired pH value range.

A contemplated emulsion is designed to be a drinkable liquid, and as such is designed to have a pH value that is pharmaceutically acceptable. Thus, the above pH range is well within the pH values exhibited by common comestibles. In addition, as discussed in detail hereinafter, a contemplated emulsion is also designed to break at a pH value of about 2.0 or less; i.e., at about the pH value of the human's or another animal's stomach.

A contemplated emulsion is a pourable liquid at normal room temperatures, e.g. about 20°–25° C. Numerically, a contemplated emulsion preferably has a viscosity of about 1 to about 1000 centipoises (cps) at a temperature of about 20°–25°, which is about the range of viscosities exhibited by water and glycerin, respectively, at those temperatures. It is more preferred that a composition viscosity be about 1 to about 200 cps at those temperatures, and most preferably about 1 to about 100 cps.

The oil phase of a contemplated emulsion is constituted by a wax matrix in which the medicament is dissolved or dispersed. The wax matrix constitutes about 3 to about 30 weight percent of an emulsion, more preferably about 5 to about 20, and most preferably about 7 to about 15 weight percent of the emulsion. Use of less than about 3 weight percent can be tolerated, but typically does not permit a sufficient loading of medicament for a commercially viable product. Use of more than 30 weight percent typically provides a viscosity that is not drinkable.

The wax matrix is a true wax; i.e., an ester of a long chain mono-fatty acid with a long chain mono-fatty alcohol, or it can be a mixture of true waxes mixed with other ingredients.

An exemplary wax is an ester formed from a $C_{14}$–$C_{22}$ monohydric alcohol and a $C_{14}$–$C_{22}$ monocarboxylic acid. A wax matrix exhibits a melting point of about 40° to about 80° C., more preferably about 45° to about 70° C., and most preferably about 60° to about 70° C.

Exemplary useful waxes include, but are not limited to myristyl palmitate, myristyl stearate, cetyl myristate, cetyl palmitate, cetyl stearate, stearyl myristate, stearyl palmirate, stearyl stearate, stearyl behenate, cetearyl behenate, behenyl behenate and mixtures thereof. Melting points for several of these materials are exemplified below.

| Wax | Length of Fatty Chain | Melting Point °C. |
| --- | --- | --- |
| Myristyl Myristate | $C_{14}$–$C_{14}$ | 37–38 |
| Myristyl Palmitate | $C_{14}$–$C_{16}$ | 44–46 |
| Myristyl Stearate | $C_{14}$–$C_{18}$ | 45–46 |
| Cetyl Myristate | $C_{16}$–$C_{14}$ | 47–49 |
| Cetyl Palmitate | $C_{16}$–$C_{16}$ | 48–50 |
| Cetyl Stearate | $C_{16}$–$C_{18}$ | 48–50 |
| Stearyl Myristate | $C_{18}$–$C_{14}$ | 47–49 |
| Stearyl Palmitate | $C_{18}$–$C_{16}$ | 54–56 |
| Stearyl Stearate | $C_{18}$–$C_{18}$ | 53–55 |

As is seen from the above table, myristyl myristate melts below about 40° C., and as such is not contemplated for use here. As is also seen from the table, several waxes that contain a $C_{14}$ alcohol or acid have appropriate melting points, and consequently, alcohol and acid chain lengths together with melting point define the wax.

Mixtures of the above waxes can be used as can natural waxes that are also mixtures so long as the melting point of the matrix is about 40° to about 80° C. The phrase "natural wax" is used here to mean a material isolated from a naturally occurring source such as beeswax or cotton wax, as compared to being synthesized in a laboratory.

One such natural wax, beeswax, is preferred here. Beeswax is a mixture of wax esters, some of whose chains contain 24 to 36 carbon atoms, and also includes about 20 weight percent hydrocarbons having odd-numbered straight carbon chains from $C_{21}$ to $C_{33}$.

Additional exemplary useful natural waxes are listed below along with their melting points.

| Natural Waxes[1] | |
| --- | --- |
| Wax | Melting Points °C. |
| Beeswax, crude | 62–66 |
| Beeswax, White, USP | 61–69 |
| Cotton | 68–71 |
| Orange peel | 44–46.5 |
| Spermaceti | 42–50 |

[1]Handbook of Chemistry and Physics, 54th ed., R. C. Weast ed., Chemical Rubber Co., CRC Press, Cleveland, 1973–1974, page C-753.

It is also preferred that the wax matrix have a mild taste or be substantially tasteless. The particularly preferred beeswax is so preferred in part because of its substantially tasteless characteristic.

The wax matrix materials are available commercially. For example, beeswax can be obtained from Frank B. Ross Co., Inc. of Jersey City, N.J. or from Strahl & Pitsch, Inc., West Babylon, N.Y. Several of the esters of $C_{14}$–$C_{22}$ alcohols and carboxylic acids are available from Croda, Inc., Parsippany, N.J.; Stepan Co., Northfield, Ill., and Koster Keunan, Inc., Sayville, N.Y.; and Scher Chemicals, Inc., Clifton, N.J. Those esters of $C_{14}$–$C_{22}$ alcohols and carboxylic acids not available commercially can be obtained from the corresponding alcohol and acid by usual esterification procedures. Further suppliers are listed in the *International Cosmetic Ingredient Dictionary*, 5th ed., Wenninger and McBiven, eds., The Cosmetic, Toiletry, and Fragrance Association, Washington, D.C.

A contemplated emulsion composition contains an emulsifying agent that provides a stable, non-settling emulsion at pH values between about 4.5 and about 8.0. That emulsifier or emulsifying agent also provides instability to the emulsion at pH values below about 2.0 so that at such pH values, the emulsion breaks or separates into its aqueous and oil phases. This breaking of the emulsion can be observed by the formation of one or more readily seen particles of wax in usual laboratory glassware upon admixture of a contemplated emulsion and an aqueous solution having a pH value of 2.0 or less that is also free of a solvent for the wax. This phenomenon is discussed in greater detail hereinafter. The emulsifier is typically present in an amount of about 2 to about 20 weight percent of the total composition.

Phospholipid emulsifying agents are particularly preferred for use in a contemplated emulsion. Phospholipids from animal sources include phosphatidylcholine, cephalin (phosphatidylethanolamine) and sphingomyelin. Plant phospholipids that include mixtures of phosphatidylcholine and cephalin as well as metallic salts of phosphatidic acids and phosphatidylinositol are referred to in the art as lecithin.

A typical phospholipid analysis of plant lecithin from one manufacturer, Central Soya, includes phosphatidylcholine at 23 percent, phosphatidylethanolamine at 20 percent, phosphatidylinositol at 14 percent and phosphatidic acid at 8 percent of the acetone insolubles of lecithin. *The Lecithin Book*, Central Soya, Chemurgy Division, Forth Wayne, Ind. (1993). A plant or vegetable lecithin is a preferred phospholipid emulsifier here, and can be commercial lecithin that includes about 60–65 percent phospholipids and about 35–40 percent plant oil, oil-free lecithin or a mixture of commercial lecithin, ethoxylated mono-diglycerides and propylene glycol. Commercial lecithin, the material containing phospholipids and plant oil will hereinafter be referred to as lecithin, in accordance with the nomenclature of the art, although phosphatidylcholine is sometimes also referred to as lecithin.

Soy lecithin is particularly preferred and can be used as the pure phospholipid (oil-free), as the soy oil/phospholipid admixture, or phospholipid/soy oil admixed with ethoxylated mono-diglycerides and propylene glycol. Cotton seed, linseed, peanut and corn lecithins are also useful as the pure phospholipid or in admixture with seed oil.

A lecithin emulsifier is present in a composition at an amount of 0.5 to about 20 weight percent. When the phospholipid is used in pure form, it is typically present at about 7 to about 20 weight percent of the total composition. A lecithin/ethoxylate/propylene glycol mixture is preferred, and when so used is preferably present at about 2 to about 10 weight percent, and more preferably at about an amount of about 5 to about 8 weight percent. Greater amounts of emulsifier are used with larger quantities of wax matrix.

A particularly preferred lecithin/ethoxylate/propylene glycol emulsifier is sold by Central Soya, Fort Wayne, Ind. under the trademark CENTROMIX® E as an amber fluid having an HLB of 12, an acid value of 17, a Brookfield viscosity at 25° C. of 6500 cps, less than one percent water, less than 0.3 percent hexane insolubles and about 50 percent acetone insolubles. CENTROMIX® E is understood to contain about 85 weight percent lecithin, about 7.5 weight percent ethoxylated mono-diglycerides and about 7.5 weight percent propylene glycol. Another useful lecithin sold under the trademark CENTROLEX® P is substantially pure lecithin; i.e., oil-free lecithin, is also available from Central Soya. This product is granular, light tan to yellow in color, is 97 percent acetone insoluble, has an HLB of about 7, and has a maximum acid value of 36 that is usually about 25. Another group of useful lecithins available from Central Soya are those materials with the designations CENTROPHASE® HR, HR2B, HR4B and HR6B, each of which is an amber liquid having about 54–62 percent acetone insolubles, viscosities of about 1800–5500 cps, acid values of about 20–23 and H to B values of about 7.5. Other lecithin products are available from American Lecithin, Danbury, Conn., and others.

The phospholipid emulsifier can also be admixed with one or more auxiliary non-ionic surfactant emulsifiers. Exemplary useful non-ionic surfactants are the ethoxylated $C_{12}$–$C_{22}$ fatty alcohols such as polyoxyethylene (2) lauryl ether, polyoxyethylene (10) myristyl ether, polyoxyethylene (25) cetyl ether, polyoxyethylene (15) stearyl ether, polyoxyethylene (30) behenyl ether and mixtures thereof such as polyoxyethylene (28) cetyl/stearyl ether. The above materials are often referred to by their International Nomenclature Cosmetic Ingredient (INCI) names as are provided in the *International Cosmetic Ingredient Dictionary*, 5th ed., Wenninger et al., eds., The Cosmetic, Toiletry, and Fragrance Association, Washington, D.C. (1993). Using INCI nomenclature, the above materials are named laureth-2, myreth-10, ceteth-25, steareth-15, beneneth-30 and ceteareth-28.

Another useful class of non-ionic surfactants is mono-$C_{12}$–$C_{18}$ fatty acid esters of hexitol anhydrides derived from sorbitol. These materials are referred to in INCI nomenclature as sorbitan esters such as sorbitan laurate, sorbitan palmitate, sorbitan oleate, sorbitan stearate and the like.

A still further class of useful non-ionic surfactants is the mixture of mono-$C_{12}$–$C_{18}$ fatty acid esters of sorbitol and sorbitan anhydrides condensed with various amounts of ethylene oxide. These materials are referred to in INCI nomenclature as polysorbate followed by a number. Exemplary of these surfactants are polysorbate 20 (a laurate ester), polysorbate 40 (a palmirate ester), polysorbate 60 (a stearate ester), and polysorbate 80 (an oleate ester). The surfactants in this group having the numbers 20, 40, 60 and 80 each has an average of 20 moles of ethylene oxide per molecule. The polysorbates designated 21, 61 and 81 contain the same esterifying fatty acid as the before mentioned polysorbate 20, 60 and 80, respectively, but polysorbates 21 and 61 contain an average of 4 moles of ethylene oxide per molecule, and polysorbate 81 contains an average of 5 moles of ethylene oxide.

A still further class of useful non-ionic surfactants is polyoxyethylene mono-$C_{12}$–$C_{22}$ fatty acid esters. These materials are referred to in INCI nomenclature as PEG, polyethylene glycol, esters in which a number is placed between the word PEG and the fatty acid name to indicate the average number of moles of reacted ethylene oxide per mole of surfactant, as was the case for the numbers used with ethoxylated fatty alcohols. Exemplary of these esters are PEG-10 laurate, PEG-20 myristate, PEG-18 palmitate, PEG-2 oleate, PEG-30 stearate, PEG-8 behenate, and PEG-15 cocoate (coconut oil fatty acids).

The above non-ionic surfactants can have an average of 2 to about 30 moles of reacted ethylene oxide per mole of surfactant. The relative amounts of reacted ethylene oxide and fatty chain are used to determine the HLB number for a given surfactant. As is well known, HLB numbers represent relative hydrophilicity/hydrophobicity values for the surfactant, with more hydrophilic materials having HLB numbers greater than about 8.

Two or more non-ionic surfactants, at least two of which have HLB numbers about 5 or more units apart are preferably used with the phospholipid emulsifier. The combined HLB of the non-ionic surfactants is preferably about 8 to about 16, and is more preferably about 12 to about 14.

The non-ionic emulsifiers are useful in providing the desired emulsification stability at higher pH values, but can provide too much stability at pH values below about 2.0. A non-ionic surfactant admixed with a phospholipid emulsifier is present at zero to about 3 weight percent of the total composition, and preferably at about zero to about 2.0 weight percent. A non-ionic surfactant is preferably used with phospholipid amounts of 0.5 to about 2 weight percent, and is preferably not used when a phospholipid emulsifier is present in excess of about 2 weight percent, unless the wax matrix is present near the high end of its range, as at about 20 to about 30 weight percent of the total emulsion.

The weight ratio of wax matrix to emulsifier is about 1:1 to about 5:1. More preferably, that ratio is about 3:2 to about 5:1. Ratios nearer to about 1:1 to about 3:2 are utilized where the wax matrix is present at about 20 weight percent or more, within the previously discussed amounts of both ingredients.

The pharmacologically active compound (medicament or drug) that is present in a contemplated composition can be any medicament that is sufficiently soluble or dispersible in the wax matrix to provide a normal dose to about 2 to about 3 times the normal (usual) dose of the medicament in the completed composition. That amount is referred to as a pharmaceutically effective amount. Inasmuch as the wax matrix is itself a hydrophobic material, hydrophobic medicaments are preferred.

Exemplary medicaments include ibuprofen, terfenadine, albuterol, trimethoprim, acetaminophen, indomethacin, dexamethasone, prednisone, prednisolone, ketoprofen, dextromethorphan, astemizole, cephalosporins, chloral hydrate, cromolyn, diphenhydramine, guaifenesin, loratadine, methylphenidate, midazolam, naproxen, penicillins and the like. These medicaments are all well known as are their usual pharmaceutically effective doses for adults and children, where appropriate. Such pharmaceutically effective amounts also can be obtained from the *Physicians' Desk Reference,* Medical Economics Co., Inc., Oradel, N.J. (1991). It is preferred that amine-containing medicaments be present as salts of organic acids rather than inorganic acids so that solubility in the matrix can be increased and solubility in water decreased. Carboxylic acid-containing medicaments are also preferably present in protonated, free acid form rather than as a salt.

The upper limit of the amount of medicament is its solubility or dispersibility in the melted wax matrix/emulsifier that is discussed hereinafter. The lower limit can also be related to solubility or dispersibility in the melted matrix/emulsifier as well as the relation of that solubility or dispersibility to a usual pharmaceutically effective amount. Thus, if the solubility of the medicament is so low that a composition cannot be prepared that provides about 0.1 milligram of medicament per five milliliter dose, the medicament is not used. The upper and lower limits are consequently limitations for commercial use.

The medicament must also be free from decomposition at a temperature below 90° C. The basis for this requirement lies in the process by which a contemplated composition is prepared, as is discussed hereinafter.

A contemplated composition can also contain zero to about 35 and more preferably about 10 weight percent of one or more additional excipients. Exemplary additional excipient materials include co-solvents such as glycerin, propylene glycol, preservatives such as a paraben or sodium benzoate, sweeteners such as saccharin, aspartame or sucrose or sorbitol syrups, with artificial sweeteners being preferred because of the relatively high concentration (greater than 10 percent) of natural sweetener required, if present as the only sweetener. Flavorants such as usually used natural or artificial cherry- or orange-flavored concentrates, and colorants are also contemplated additional excipients. The excipients are part of the water phase of the emulsion.

These excipients are referred to as being "additional" because they are inactive as medicaments as are the water, wax matrix and emulsifier, which can also be viewed as excipients. Thus, the "additional" excipients are present in addition to water, the wax matrix and emulsifier.

B. Controlled Release Process

As is illustrated in the specific examples that follow, a contemplated emulsion breaks at a pH value below about 2.0 to separate the oil and water phases and form a composition in which the oil phase coalesces into a relatively few large particles present in an aqueous medium, the particle size depending upon the severity of agitation. For example, a 5 mL dose of the emulsion on being placed into simulated stomach acid (pH 1.2) can form one to about twenty waxy pieces if not agitated. Thus, where the oil phase constitutes about 20 percent of the emulsion, a single coalesced piece would have a volume of one mL.

Once in the acidic environment of the stomach, a contemplated liquid emulsion composition de-emulsifies (breaks or separates) to form relatively large waxy pieces. Breakage of the emulsion typically occurs in a matter of a few seconds to few minutes; i.e., almost immediately, and before stomach emptying can occur. Those waxy pieces contain the medicament that can be released from the formed pieces in the stomach or can be released after exit from the stomach into the intestines where the pH value is higher. Release of the medicament can also occur both in the stomach and intestinal tract. Regardless of where release occurs, that release is relatively prolonged as compared to the release obtained if the medicament were dissolved or provided as a suspension in an aqueous medium. Thus, the human or other recipient can drink the liquid composition and obtain an orally administered controlled release of the selected medicament as has heretofore been only available from a solid dosage form.

A process for administering a controlled release medicament composition is also contemplated. A mammalian patient in need of the medicament such as a child or adult human, a laboratory animal such as a rabbit, mouse or rat, or a veterinary animal such as a dog, cat, horse, bovine or sheep is a contemplated recipient.

A before-described controlled release liquid aqueous emulsion composition is provided and is administered to the recipient perorally, e.g., by drinking. The previously discussed preferences as to the controlled release liquid composition apply as well in the use of a composition.

In preferred practice, the medicament is present in a contemplated emulsion at about two to about three times the normal dose, and as a result of the controlled release of that medicament to the patient's body, a contemplated emulsion need only be administered about one-half to one-third as often as an immediate release preparation. Put differently, where dosing is repeated, a contemplated emulsion composition can be administered at intervals that are about two to about three times longer than the usual intervals. Even where usual dosages are utilized, the medicament is released over a relatively longer time period than a usual immediate release dosage form.

Inasmuch as the wax matrix is preferably selected for its bland, substantially tasteless characteristic, and the fact that the often bad tasting medicament is dissolved in the wax matrix of the oil phase of the emulsion, a usual emulsion has little if any taste so recipients have little difficulty or problem with drinking and swallowing a composition because of its taste. As already noted, sweeteners and taste-enhancers can also be and preferably are added to an emulsion to improve palatability.

C. Process of Preparation

A process for preparing a contemplated oil-in-water emulsion controlled release composition is also contemplated. In accordance with a contemplated process, (a) a homogeneous molten admixture at a temperature below about 85° C. is provided. The molten admixture contains (i) a wax matrix having dissolved or dispersed therein (ii) a pharmaceutically effective amount of a pharmacologically active compound and (iii) an emulsifier. The contemplated wax matrix is a wax having a melting point of about 40° to about 80° C. The ratio of wax matrix to emulsifier is about 1:1 to about 5:1, to about 3:2 to about 5:1. The pharmacologically active compound utilized is free from decomposition below about 90° C.

(b) A water (aqueous) phase is provided having a temperature about 5° C. higher than that of the molten admixture. The pH value of the water phase is adjusted if necessary to provide an emulsion composition having a pH value of about .4.5 to about 8.0. Preferably, no pH adjustment is needed.

(c) The molten admixture as oil phase is microemulsified with a sufficient amount of the water (aqueous) phase at the temperature of the water phase to form a stable, non-settling emulsion in which the aqueous phase is external and in which the oil phase particles have an average size of about 100 nm to about 250 nm. The relative amounts of aqueous and oil phase present at this stage are within about 20 percent of the final percentages desired.

(d) The resultant emulsion is then cooled to a temperature of about 10° to about 25° C.

(e) Zero to about 35, and more preferably to about 10 percent additional excipient and sufficient water are admixed, and the pH value is adjusted, if necessary, such that the formed pharmaceutical emulsion composition has a viscosity at 20°-25° C. of about 1 to about 1000 cps, a pH value of about 4.5 to about 8.0, a water phase that constitutes at least 25 and more preferably at least 50 weight percent of the total composition, and an oil phase that contains (i) the wax matrix constituting about 3 to about 30 weight percent of the total composition, (ii) the emulsifier constituting about 1 to about 20 weight percent of the total composition, and (iii) an effective amount of the pharmacologically active compound.

The temperature of the molten admixture can be a function of the specific wax matrix and specific emulsifier utilized. The wax matrix is usually melted first and the admixed with the medicament until a homogeneous admixture is obtained. The emulsifier is then added with further mixing until a further homogeneous admixture is obtained.

The molten admixture can have a temperature as low as the melting point (range) of the wax matrix up to about 85° C. It is preferred, however, that the molten admixture have a temperature of about 60° to about 80° C., with a temperature of about 60° to about 70° C. being more preferred.

The weight ratio of wax matrix to phospholipid emulsifier is about 3:2 to about 5:1. Again, this ratio is a function of the specific materials used, the amount of wax matrix present in a given composition and whether a pure phospholipid such as CENTROLEX® P or a phospholipid/seed oil ethoxylated mono-diglyceride/propylene glycol mixture emulsifier such as a CENTROMIX® E, is used, with more of the pure phospholipid being required than the mixture. More preferred weight ratios of wax matrix to phospholipid emulsifier are about 2:1 to about 4:1 for the more preferred amounts of wax matrix.

The water phase that is microemulsified with the molten admixture is at a temperature that is at least about 5° C. higher than that of the molten admixture. The water phase can thus have a temperature of up to about 90° C., and as low as about 45° C., where a low-melting waxy matrix is used. Inasmuch as the molten admixture is usually used at a temperature of about 60° to about 80° C., the water phase is usually at a temperature of about 65° to about 85° C.

The medicament dissolved or dispersed in the molten admixture must not decompose at a temperature below about 90° C. because the molten admixture can have a temperature up to about 85° C., the aqueous phase is provided at a temperature about 5° C. higher than the molten admixture and that temperature is used during microemulsification. It is not necessary for the medicament to also be independently molten at the temperature of the molten admixture as the medicament is dissolved or dispersed therein.

The aqueous phase typically contains only water at the time of admixture with the oil phase molten admixture because preservatives, sweeteners and flavorants frequently are sensitive to the relatively elevated temperatures utilized during microemulsification. Materials that are insensitive to the temperatures utilized such as propylene glycol or glycerin can be present in the heated aqueous phase.

The molten admixture and aqueous phase are microemulsified at the temperature of the aqueous phase. A microfluidizer Model 110T available from Microfluidics Corporation, Newton Mass. is a preferred machine for use in laboratory preparation, whereas a Union Homogenizer available from Union Pump Co., North Andover, Mass. can be used for large scale manufacture. These machines provide high pressure homogenization that provides an opaque microemulsion whose particles have an average size of about 100 nm to about 250 nm, and more preferably about 150 nm to about 200 nm.

The warmed emulsion is then cooled to a temperature of about 10° to about 25° C. (ambient room temperature) and further water and additional excipients are added if desired so that the composition contains the before discussed constituent amounts and exhibits the desire pH value and viscosity.

The previously discussed preferences as to constituents, pH value, viscosity and the like of a composition also hold for a process for preparing such a composition.

D. Best Mode for Carrying Out the Invention

Example 1

Emulsion Preparation

A series of contemplated emulsions was prepared as discussed below, using the relative compositions of materials shown in Table 1, below.

TABLE 1

CONTROLLED RELEASE COMPOSITIONS

| | Composition No. | | | | | |
|---|---|---|---|---|---|---|
| Component | 1 | 2 | 3 | 4 | 5 | 6 |
| Wax Matrix | | | | | | |
| Beeswax | 10 | 10 | 10 | 10 | — | — |
| Kester ® 48[1] | — | — | — | — | 10 | — |
| Kester ® 62[2] | — | — | — | — | — | 10 |
| Medicament | | | | | | |
| Ibuprofen | 1.0 | — | — | — | 1.0 | 1.0 |
| Albuterol | — | 0.5 | — | — | — | — |
| Trimethoprim | — | — | 1.0 | — | — | — |
| Indomethocin | — | — | — | 1.0 | — | — |

TABLE 1-continued

CONTROLLED RELEASE COMPOSITIONS

| | Composition No. | | | | | |
|---|---|---|---|---|---|---|
| Component | 1 | 2 | 3 | 4 | 5 | 6 |
| Emulsifier | | | | | | |
| CENTROMIX® E[3] | 0.57 | 0.57 | 0.57 | 0.57 | 1.2 | 1.2 |
| CENTROLEX® P[4] | — | — | — | — | 0.8 | 0.8 |
| SPAN® 60[5] | 1.14 | 1.14 | 1.14 | 1.14 | — | — |
| TWEEN® 20[6] | 0.29 | 0.29 | 0.29 | 0.29 | — | — |
| Further Excipients | | | | | | |
| Propylene glycol | 5 | 5 | 5 | 5 | 5 | 5 |
| Methyl Paraben[7] | 0.5 | 0.5 | 0.5 | 0.5 | 0.5 | 0.5 |
| Propyl Paraben[8] | 0.1 | 0.1 | 0.1 | 0.1 | 0.1 | 0.1 |
| Water | qs 100 | qs 100 | qs 100 | qs 100 | qs 100 | qs 100 |
| pH value | 5.0 | 6.0 | 6.8 | 5.2 | 4.8 | 5.5 |
| Viscosity (cps) @ 25° C. | <10 | <10 | <10 | <10 | <10 | <10 |

[1]Kester™ 48 is cetyl palmitate that is available from Koster Keunan, Inc., Sayville, NY.
[2]Kester™ 62 is cetyl/stearyl behenate that is also available from Koster Keunan.
[3]CENTROMIX® E is a mixture of about 85 percent lecithin, 7.5 percent ethoxylated mono-diglycerides and 7.5 percent propylene glycol, available from Central Soya, Fort Wayne, IN.
[4]CENTROLEX® P is substantially pure lecithin, available from Central Soya.
[5]SPAN® 60 is sorbitan stearate, a monoester of stearic acid and hexitol anhydrides derived from sorbitol that is available from ICI Surfactants-Personal Care/U.S., Wilmington, DE.
[6]TWEEN® 20 is a mixture of laurate esters of sorbitol and sorbitol anhydrides condensed with about 20 moles of ethylene oxide that is available from ICI Surfactants-Personal Care/U.S.
[7]Methyl paraben is methyl p-hydroxybenzoate.
[8]Propyl paraben is n-propyl p-hydroxybenzoate A microfluidizer Model 110T microemulsifier (homogenizer) from Microfluidics Corporation, Newton, Mass. is preheated by the circulation of water at a temperature near boiling for 30 minutes. The wax matrices are separately melted, with that of Composition Nos. 1–4 being maintained at 65° C., Composition No. 5 at 45° C., and Composition No. 6 at 60° C.

The medicament is admixed with the gently stirring melted wax over a time period of about five minutes, with the resulting admixture being stirred gently to provide homogeneity and while maintaining the above temperature. The emulsifiers are then slowly added, with the phospholipid CENTROMIX® E being added first, followed by the auxiliary sorbitol derivative emulsifiers, if used, and then CENTROLEX® P, when used. Again, the resulting molten admixture is gently stirred to homogeneity while substantially maintaining the above temperatures to complete the oil phase of the emulsion.

The required amount of water-propylene glycol mixture is heated in a separate container to a temperature about 5° C. warmer than the melted wax. Once the water-propylene glycol mixture is at the desired temperature, the recirculating, heating water is drained from the microemulsifier, and the preheated oil and aqueous phases are added to the reservoir of the microemulsifier. The microemulsifier is turned on in a recirculation mode for about 15 minutes. The resulting emulsions are thereafter collected in suitable containers, and cooled with gentle stirring to ambient room temperature, at which time the methyl and propyl paraben preservatives are added with further stirring.

Example 2

Controlled Release Ibuprofen and Trimethoprim Beeswax Emulsions

A. Preparation

Beeswax emulsions were prepared using a weakly acidic (ibuprofen) and weakly basic (trimethoprim) medicaments drug in order to study release behavior at various pH values. Procedures discussed in Example 1 were followed.

Ibuprofen and trimethoprim were mixed with melted beeswax along with soy lecithin; (CENTROMIX® E) present at 10 and 7 percents, respectively, of the finally formed emulsion, to form the oil phase. Either ibuprofen (200 mg/20 mL) or trimethoprim (200 mg/20 mL) was added to the formulation to form the oil phase. This oil phase was then dispersed in the aqueous phase using a Microfluidizer. Emulsions with this drug loading were subjected to dissolution studies, as discussed below.

The emulsions had very low viscosities and were off-white in color. The ibuprofen emulsion had a slightly acidic pH value (5.0) and the trimethoprim emulsion had a slightly alkaline pH value (6.8) as compared to that of a similar emulsion containing no medicament (placebo) whose pH value was 6.3. The particle size of these emulsions ranged from 150 nm to 210 nm. The emulsions did not have any offensive taste and were stable at room temperature for over three months. Viscosities were less than 10 cps at 25° C.

B. Dissolution Studies

An in vitro dissolution study was carried out at pH values of 1.2, 2.5, 4.5, 7.0 and 7.5. Simulated gastric and intestinal fluids were prepared according to *United States Pharmacopeia XXII*, USP Convention, Inc., Rockville, Md., 1990, pages 1788–1789 (hereinafter USP) without the addition of enzymes, and mixed to derive the desired pH valued solutions.

Because these emulsions break into a waxy matrix and aqueous phase at pH less than 2.0, the dissolution study at pH 1.2 was readily carried out. However, as the emulsion dispersed in dissolution media with pH values greater than 2 producing turbid solutions, the dissolution method was modified.

The emulsions for studies at pH values above 2 were therefore first broken by admixture in 10 mL of 0.1N HCl. The resulting mixture was then transferred into the dissolution vessel. The pH value of the dissolution medium was maintained slightly toward the alkaline side to accommodate the decrease in pH upon addition of 10 mL of 0.1N HCl. This pH value drop was studied in blank solutions for pH 2.5, 4.5, 7.0 and 7.5. Adjustments in pH were made to accommodate the pH value drop so that the final pH value remained close to 2.5, 4.5, 7.0 and 7.5.

USP dissolution apparatus II (paddle) USP, ibid., was used to study the dissolution. The water bath temperature was maintained at 37°±0.5° C., and paddle speed was adjusted to 50 rpm.

Figure 1:
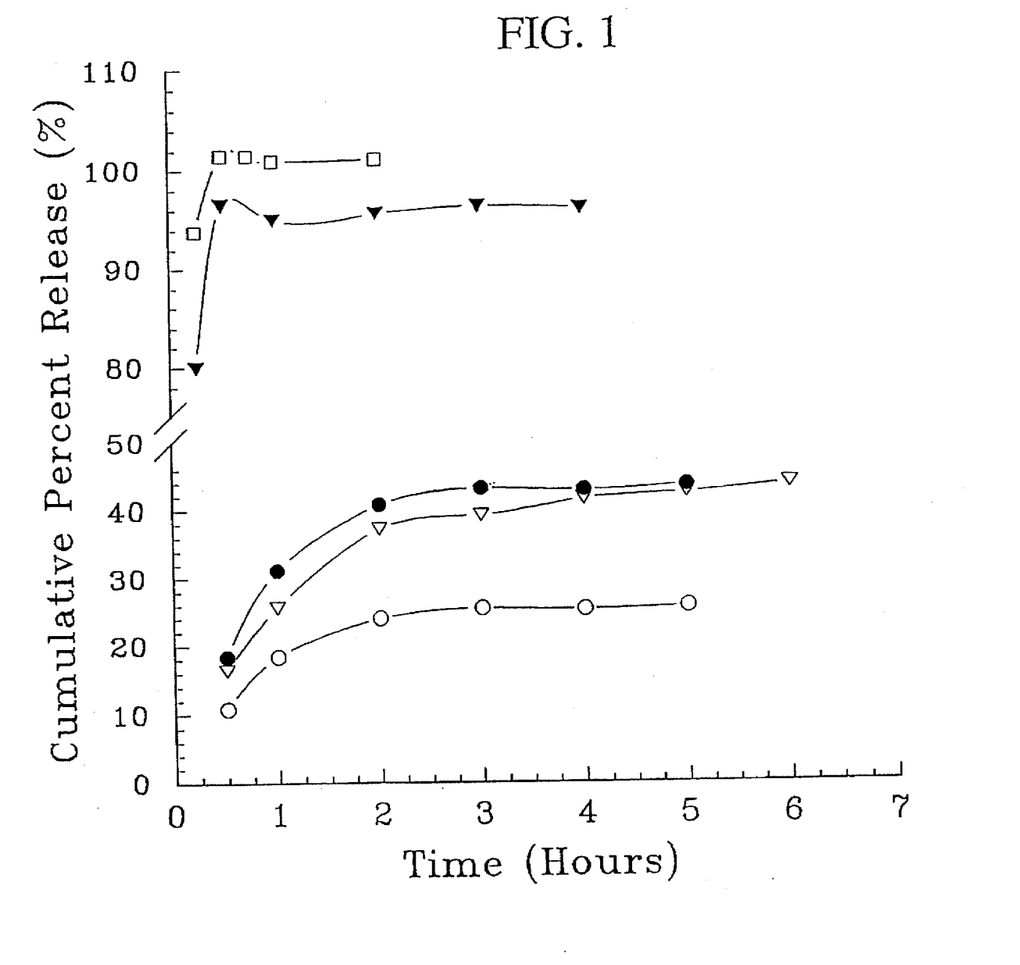
FIG. 1 is a graph showing the comparative percent release over time of ibuprofen immediate release tablets in simulated gastric and intestinal fluids at pH 1.2 (open circles), pH 2.5 (closed circles), pH 4.5 (open inverted triangles), pH 7.0 (closed inverted triangles), and pH 7.5 (open squares)
Figure 2:
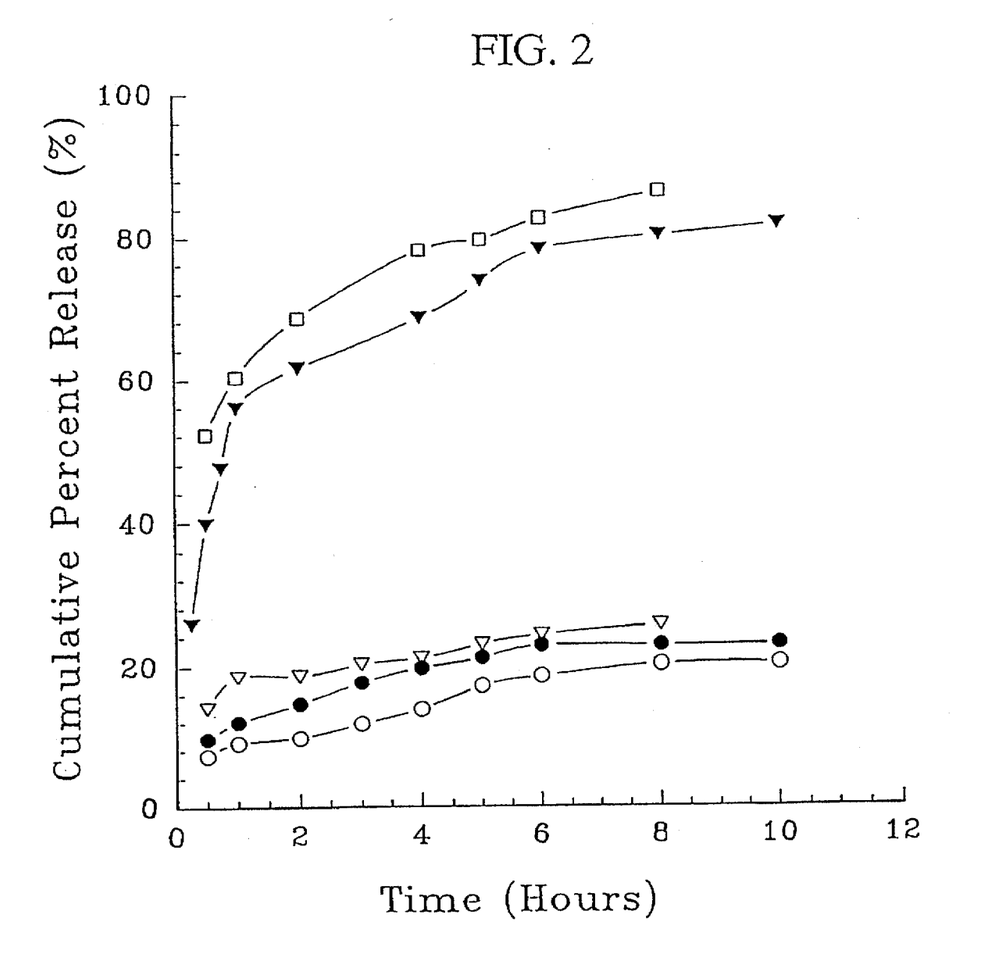
FIG. 2 is a graph showing the comparative percent release over time of ibuprofen from a contemplated emulsion upon breaking of the emulsion and subsequent admixture of the broken emulsion with simulated gastric and intestinal fluids using the pH values and symbols of FIG. 1.
Figure 3:
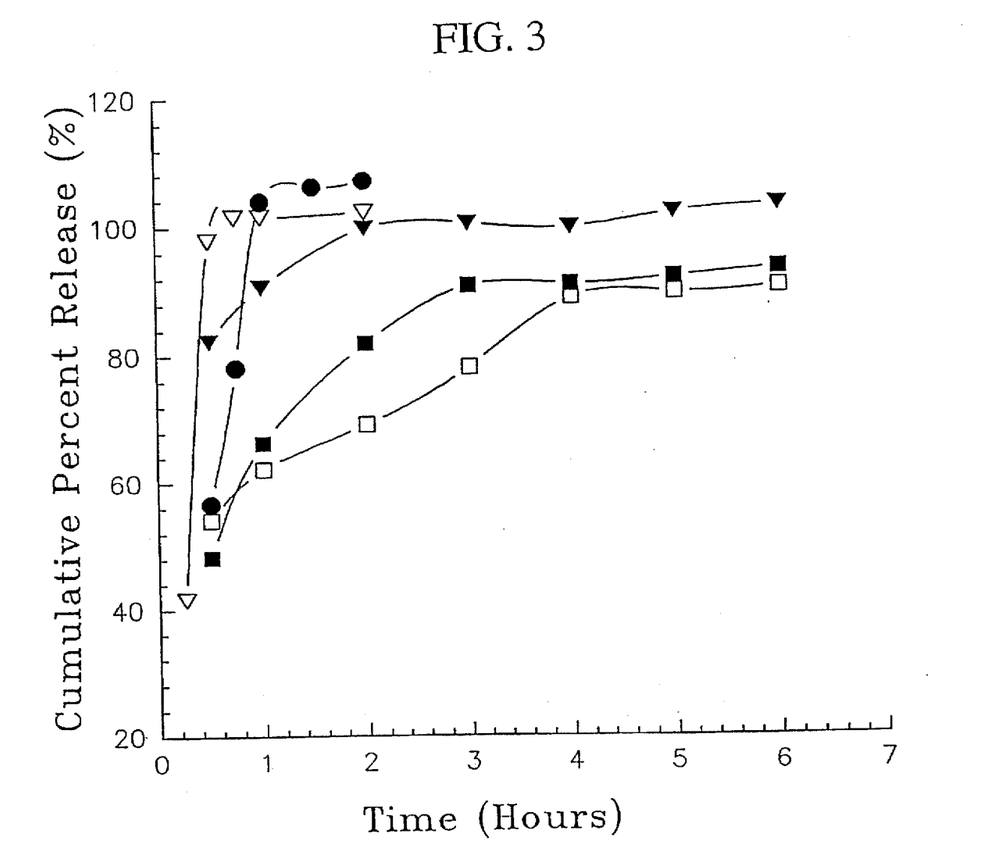
FIG. 3 is a graph similar to that of FIG. 1 showing the comparative percent release over time of trimethoprim immediate release tablets under conditions similar to those of FIG. 1 at pH 1.2 (closed circles), pH 2.5 (open inverted triangles), pH 4.5 (closed inverted triangles), pH 7.0 (open squares) and pH 7.5 (closed squares)
Figure 4:
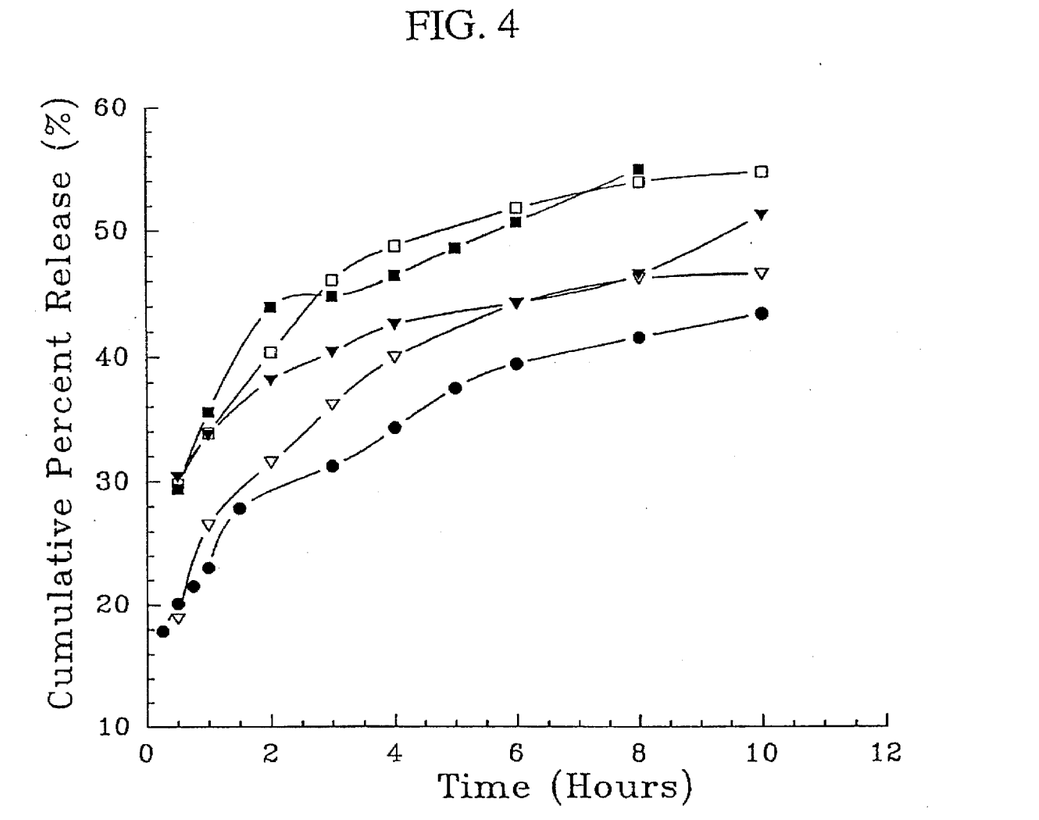
FIG. 4 is a graph similar to that of FIG. 2 showing the comparative percent release over time of trimethoprim from a contemplated emulsion upon breaking of the emulsion and subsequent admixture of the broken emulsion with simulated gastric and intestinal fluids using the pH values and symbols of FIG. 3.

Data for dissolution of commercially available ibuprofen tablets (200 mg; Dixon-Shane, Inc., Lot #3418) and trimethoprim tablets (200 mg; Rugby Laboratories, Inc., Lot #13853) in aqueous solutions at pH values of 1.2, 2.5, 4.5, 7.0 and 7.5 are illustrated in FIGS. 1 and 3, respectively. The data of FIGS. 2 and 4 illustrate the release of ibuprofen and trimethoprim, respectively, from emulsions first broken in 0.1N HCl, and then transferred to solutions at the indicated pH values, except for the pH 1.2 study.

In general, controlled release was observed from the emulsions in comparison to commercially available immediate release tablets. The dissolution data for the emulsions suggested enteric type release for ibuprofen emulsions and slow release for trimethoprim emulsions. The enteric type release was due to the inherent solubility of drug at alkaline pH values and solubilization of wax particles. Because trimethoprim is more soluble at acidic pH values, its release was inhibited by the wax matrix, as the wax is insoluble in acidic medium. The release of drug through the wax in acidic medium seemed to be primarily due to diffusion. The drug release data from emulsions appears to fit a first order release kinetics model.

C. Methods Utilized in Dissolution Studies

1. Calibration Plots

Calibration plots of ibuprofen, USP and trimethoprim, USP in dissolution fluids of pH 1.2, 2.5, 4.5, 7.0 and 7.5 were prepared over the concentration range of 5 to 25 µg/mL using wavelengths of 220 nm and 270 nm, respectively. Calibration curves were obtained by plotting absorbance versus concentration. The slope, intercept and correlation coefficient were obtained by linear regression of absorbance versus concentration. The correlation coefficient of the calibration plots were used to evaluate the goodness of fit to Beer's law.

2. Dissolution of Immediate Release Ibuprofen 200 mg and Trimethoprim 200 mg Tablets Dissolution study was carried out using USP dissolution apparatus II (paddle method). Appropriate amounts of dissolution fluid were prepared for dissolution at a particular pH value. Dissolution volumes of 900 mL were used at 37°±0.5° C., with a spindle speed set at 50 rpm. Immediate release tablets of both drugs were tested at pH 1.2, 2.5, 4.5, 7.0 and 7.5. In case of ibuprofen tablets, the samples were drawn at intervals of 15 minutes for dissolution at higher pH values (4.5, 7.0, 7.5) and for trimethoprim at low pH values (1.2, 2.5, 4.5), because the solubility of the two drugs is pH dependent. Standard curves were prepared in each medium and a working standard was chosen to calculate the release of the drug from the tablets. Dissolution was carried out until three consecutive samples provided a constant absorbance reading. Using the known concentration and absorbance of a working standard and knowing the absorbance of samples, the amount released was calculated at a particular sampling time.

3. In vitro Dissolution Study (a) Dissolution Media

Simulated gastric fluid and simulated intestinal fluid were prepared as described in USP without the addition of enzymes. Required volumes of five different media (pH 1.2, 2.5, 4.5, 7.0, 7.5), were prepared by mixing definite proportions of both gastric fluid (pH 1.2) and intestinal fluid (pH 7.5) as shown in the table, below.

| | Extracting Fluids | |
|---|---|---|
| Extracting pH | Simulated gastric fluid TS, ml | Simulated intestinal fluid TS, ml |
| 1.2 | 100 | 0 |
| 2.5 | 46 | 54 |
| 4.5 | 39 | 61 |
| 7.0 | 17.5 | 82.5 |
| 7.5 | 0 | 100 |

Source: United States Pharmacopeia XXII, USP Convention, Inc., Rockville, MD, 1990, pages 1788–1789.

(b) Dissolution of Microfluidized Beeswax-Ibuprofen and Beeswax-Trimethoprim Emulsions In vitro dissolution studies were carried out using USP dissolution apparatus II (paddle method) to determine drug release pattern. Appropriate amounts of dissolution fluid were prepared for dissolution at a particular pH value. A dissolution volume of 900 mL was used at (37°±0.5° C.), and spindle speed was set at 50 rpm. Separate emulsions of both drugs were studied at pH values of 1.2, 2.5, 4.5, 7.0 and 7.5. Samples were drawn at intervals of 15 minutes for dissolution at higher pH values (4.5, 7.0, 7.5) for the beeswax-ibuprofen emulsions, and for beeswax-trimethoprim emulsions at low pH values (1.2, 2.5, 4.5). Standard curves were prepared in each medium and a working standard was chosen to calculate the drug release. Dissolution was carried out until three consecutive samples provided a constant absorbance reading.

Each sample was filtered through a 0.45 µm syringe filter and diluted with the dissolution medium. Samples were read at appropriate maximum wavelengths using an ultraviolet spectrophotometer. Using the known concentration and absorbance of a working standard, and knowing the absorbance of samples, the amount of drugs released was calculated at a particular sampling time.

4. Determination of Total Drug Content

A known quantity of each emulsion (trimethoprim and ibuprofen) was mixed with 0.1N HCl and phosphate buffer pH 7.2, respectively. A placebo emulsion was prepared and mixed with 0.1N HCl and phosphate buffer pH 7.2, to serve as a blank. The mixtures were mixed well and centrifuged. Immediate release tablets of ibuprofen and trimethoprim (equivalent to the amount present in emulsion samples) were crushed into fine powders in a mortar and pestle. Accurately weighed quantities of ibuprofen and trimethoprim tables were dissolved in 0.01N HCl and phosphate buffer pH 7.2, respectively, and mixed well.

Example 3

Controlled Release Ibuprofen and Albuterol Emulsions

A. Preparation

Beeswax and three sythetic wax (Kester™ 48, Kester™ 62 and Kester™ 72) emulsions were prepared using a weakly acidic (ibuprofen) and weakly basic (albuterol) medicaments drug in order to study release behavior at various pH values. Procedures discussed in Example 1 and 2 were followed.

Ibuprofen and albuterol were mixed with the melted wax along with an appropriate emulsifier with the wax and emulsifier present at 10 and 2 percents, respectively, of the finally formed emulsion, to form the oil phase. The content of the emulsifier varied with the wax used. The preferred emulsifier HLB value for each was as follows: beeswax (8.2–9.9), Kester™ 48 (8.2–9.9), Kester™ 62 (about 9.9) and Kester™ 72. (about 8.2). The emulsifier blend contained Centromix® E and a combination of non-ionic surfactant emulsifiers (Spans® and Tweens®) that provided the preferred emulsifier HLB value.

Either ibuprofen (100 mg/10 mL) or albuterol (4 mg/10 mL) was added to the formulation to complete formation of the oil phase. This oil phase was then dispersed in the aqueous phase using a Microfluidizer. Emulsions with this drug loading were subjected to dissolution studies, as discussed below.

The emulsions had very low viscosities (less than 10 cps at 20° C.) and were off-white in color. The ibuprofen emulsions each had slightly acidic pH values between 4.5 and 5.0, whereas the albuterol emulsions had slightly alkaline pH values between 5.8 and 6.1 as compared to pH values of a similar emulsion containing no medicament (placebo) whose pH values were between 5.4 and 6.0. The particle size of these emulsions ranged from 150 nm to 210 nm. The emulsions did not have an offensive taste and were stable at room temperature for over three months.

B. Dissolution Studies

In vitro dissolution studies were carried out at pH values of 1.2, 4.5 and 7.5. Simulated gastric and intestinal fluids were prepared according to *United States Pharmacopeia*

XXII, USP Convention, Inc., Rockville, Md., 1990, pages 1788–1789 (hereinafter USP) without the addition of enzymes, and mixed to derive the desired pH valued solutions.

Because these emulsions break into a waxy matrix and aqueous phase at a pH value less than about 2.0, the dissolution study at pH 1.2 was readily carried out. However, as the emulsion dispersed in dissolution media with pH values greater than 2 producing turbid solutions, the dissolution method was modified.

The emulsions for Studies at pH values above 2 were therefore first broken by admixture in 10 mL of 0.1N HCl. The resulting mixture was then transferred into the dissolution vessel. The pH value of the dissolution medium was maintained slightly toward the alkaline side to accommodate the decrease in pH upon addition of 10 mL of 0.1N HCl. This pH value drop was studied in blank solutions for pH 4.5 and 7.5. Adjustments in pH were made to accommodate the pH value drop so that the final pH value remained close to 4.5 and 7.5.

USP dissolution apparatus II (paddle) USP, ibid., was used to study the dissolution. The water bath temperature was maintained at 37°±0.5° C., and paddle speed was adjusted to 50 rpm.

Data for dissolution of commercially available immediate release ibuprofen tablets (100 mg; Pediaprofen®) and a commercially available dual dose albuterol tablets (Proventil™ repetabs) in aqueous solutions at pH values of 1.2, 4.5 and 7.5 were obtained. The Pediaprofen release was similar to the data shown in FIG. 1 for pH values of 1.2, 4.5 and 7.5. The Proventil™ repetabs immediately released their first dose at pH 1.2, 4.5 and 7.5. However, the second dose of albuterol from the Proventil® repetabs was only observed at pH 1.2 after 6 hours. Except for the pH 1.2 study, the emulsions were first broken in 0.1N HCl, and then transferred to solutions at the indicated pH values.

In general, controlled release of ibuprofen was observed from the Beeswax, Kester™ 48, Kester™ 62 and Kester™ 72 emulsions in comparison to commercially available immediate release tablets. The release rates were dependant upon the pH value. The drug was released more slowly at pH 4.5 and 7.5.

In the Kester™ 72 emulsion, release at pH 4.5 and 7.5 were slow and controlled, a plateau was reached after six hours. However, at pH 1.2, 20 percent (20%) of the drug was released and a plateau was reached after 2 hours.

Controlled release of albuterol was observed from each of the emulsions at all three pH values. Whereas the commercially available dual dose Proventil™ repetabs only released their second dose at pH 1.2.

Release from the beeswax emulsion was slow and incomplete over a twelve hour period, possibly due to low drug loading.

Release of albuterol from the Kester™ 48 emulsion varied with pH value. Release at pH 1.2 was slow, with 60 percent (60%) being released over twelve hours. At pH 4.5 and 7.5, most drug was released at six and four hours, respectively, probably due to saponification of the wax matrix at alkaline pH. Drug release appeared to follow first order kinetics.

Release of albuterol from the Kester™ 62 emulsion also varied with pH value. Release at pH 1.2 was slow and incomplete with most of drug being released in the first four hours. Release at pH 4.5 and 7.5 was higher, possibly due to the loss of integrity of the wax matrix. Release at pH 4.5 and 7.5 appeared to follow first order kinetics.

Release of albuterol from the Kester™ 72 emulsion was slow and incomplete at pH 1.2. At pH 4.5 and 7.5 most of the drug was released in four and three hours respectively.

The dissolution data for the emulsions suggested enteric type release for ibuprofen emulsions and slow release for albuterol emulsions. The enteric type release was due to the inherent solubility of drug at alkaline pH values and solubilization of wax particles. Because albuterol is more soluble at acidic pH values, its release was inhibited by the wax matrix, as the wax is insoluble in acidic medium. The release of drug through the wax in acidic medium seemed to be primarily due to diffusion.

C. Methods Utilized in Dissolution Studies

1. Calibration Plots

Calibration plots of ibuprofen, USP and albuterol, USP in dissolution fluids of pH 1.2, 4.5 and 7.5 were prepared as dicussed in Example 2.

2. Dissolution of Immediate Release Ibuprofen 100 mg and Albuterol Dual Dose Tablets Dissolution study was carried out as discussed o in Example 2. Immediate release tablets of ibuprofen and dual dose tablets of albuterol were tested at pH 1.2, 4.5 and 7.5. In case of ibuprofen tablets, the samples were drawn at intervals of 15 minutes for dissolution at higher pH values (4.5, 7.5) and for albuterol at low pH values (1.2, 2.5, 4.5), because the solubility of the two drugs is pH dependent. Standard curves were prepared as discussed in Example 2.

3. In vitro Dissolution Study

The In vitro dissolution study was carried out in three different media (pH 1.2, 4.5 and 7.5) using the procedures discussed in Example 2.

4. Determination of Total Drug Content

The total drug content was determined as discussed in Example 2.

Example 4

In Vivo Study in Rabbits of Ibuprofen Beeswax Emulsions

An In vivo study in rabbits using the ibuprofen emulsions of Example 3 was carried out. This study showed modified slow release of ibuprofen from the beeswax, Kester™ 48 and Kester™ 62 emulsions. The Kester™ 62 emulsion exhibited highest bioavailability and slowest release, followed by the beeswax and Kester™ 48 emulsions.

The particular Kester™ 72 emulsion used here did not exhibit controlled release. Rather, drug release was similar to release from Pediaprofen® immediate release tablets. It is believed that the failure of the Kester™ 72 emulsion was due to the specific formulation used as well as the drug and animal model chosen.

The foregoing is intended as illustrative of the present invention but not limiting. Numerous variations and modifications can be effected without departing from the true spirit and scope of the invention.

We claim:

1. A controlled release pharmaceutical composition including a water phase and an oil phase, said composition comprising an oil-in-water emulsion having an average oil particle size of about 100 nm to about 250 nm, a pH value of about 4.5 to about 8.0 and a viscosity at 20°–25° C. of 1 to about 1000 cps, said water phase constituting at least 25 weight percent of the total composition, said oil phase comprising a wax matrix that is a wax having a melting point of about 40° to about 80° C. that is present in an amount of about 3 to about 30 weight percent of the total composition and in which is dissolved or dispersed a pharmaceutically effective amount of a pharmacologically active compound that is free from decomposition at a temperature below about 90° C., said oil and water phases being emulsified by an emulsifying agent that provides freedom from phase separation at a pH value of about 4.5 to about 8, while also providing phase separation at a pH value below about 2.0, and is present at about 2 to about 20 weight percent of the total composition, said composition containing zero to about 35 weight percent of the total composition additional excipient.

2. The pharmaceutical composition according to claim 1 wherein said wax matrix is present in an amount of about 5 to about 20 weight percent of the total composition, and has a melting point of about 45° to about 70° C.

3. The pharmaceutical composition according to claim 1 wherein said water and oil phases are emulsified by an emulsifier comprising 0.5 to about 20 weight percent of the total composition phospholipid and zero to about 3 weight percent of the total composition non-ionic surfactant having an HLB of about 8 to about 16.

4. The pharmaceutical composition according to claim 3 wherein said phospholipid emulsifier is lecithin.

5. A process for administering a controlled release medicament composition to a recipient in need thereof that comprises the steps of
   (a) providing a liquid pharmaceutical composition of claim 1; and
   (b) perorally administering said liquid composition to said recipient.

6. A controlled release pharmaceutical composition that comprises an oil-in-water emulsion including a water phase and an oil phase, said emulsion being stable at a pH value of about 5.5 to about 7.5 but separating at a pH value less than about 2.0 into water and oil phases, said composition having an average oil phase particle size of about 100 nm to about 250 nm, a pH value of about 5.5 to about 7.5 and a viscosity at 20°–25° of about 1 to about 200 cps, said water phase constituting at least 50 weight percent of the total composition, said oil phase comprising a wax having a melting point of about 45° to about 70° C. and present in an amount of about 5 to about 20 weight percent of the total composition, said wax having dissolved or dispersed therein a pharmaceutically effective amount of a pharmacologically active compound that is free from decomposition at a temperature below about 90° C., said oil and water phases being emulsified by an emulsifier present in a total amount of about 2 to about 20 weight percent of the total composition that comprises 0.5 to about 20 weight percent of the total composition phospholipid and zero to about 3 weight percent of the total composition of a non-ionic surfactant having an HLB of about 8 to about 16, said composition containing zero to about 10 weight percent of the total composition additional excipient.

7. The pharmaceutical composition according to claim 6 wherein said wax is selected from the group consisting of beeswax and an ester of a $C_{14}$–$C_{22}$ fatty acid and a $C_{14}$–$C_{22}$ fatty alcohol.

8. The pharmaceutical composition according to claim 7 wherein said wax is beeswax.

9. The pharmaceutical composition according to claim 8 wherein said viscosity is about 1 to about 100 cps.

10. The pharmaceutical composition according to claim 6 wherein said wax is present at about 7 to about 15 weight percent of the total composition.

11. A process for administering a controlled release medicament composition to a recipient in need thereof that comprises the steps of
   (a) providing a liquid pharmaceutical composition of claim 7; and
   (b) perorally administering said liquid composition to said recipient.

12. The pharmaceutical composition according to claim 6 wherein said phospholipid is selected from the group consisting of lecithin, oil-free lecithin and lecithin additionally containing ethoxylated mono-diglycerides and propylene glycol.

13. The pharmaceutical composition according to claim 6 wherein said non-ionic surfactant is a mixture of non-ionic surfactants two of whose HLB values differ by about 5 or more.

14. The pharmaceutical composition according to claim 6 wherein said emulsifier contains zero non-ionic surfactant and about 2 to about 10 weight percent of the total composition of said phospholipid.

15. The pharmaceutical composition according to claim 6 wherein said phospholipid is a lecithin additionally containing ethoxylated mono-diglycerides and propylene glycol.

16. A controlled release pharmaceutical composition that comprises an oil-in-water emulsion having water and oil phases, said emulsion being stable at a pH value of about 5.5 to about 7.5, but separating into oil and water phases at a pH value less than about 2.0, said composition having an average oil phase particle size of about 100 nm to about 250 nm, a pH value of about 5.5 to about 7.5 and a viscosity at 20°–25° C. of about 1 to about 100 cps, said water phase constituting at least 70 weight percent of the total composition, said oil phase ,comprising beeswax that is present in an amount of about 7 to about 10 weight percent of the total composition and having dissolved therein a pharmaceutically effective amount of a pharmacologically active compound that is free from decomposition at a temperature below about 90° C., said oil and water phases being emulsified by a phospholipid emulsifier that is lecithin admixed with ethoxylated mono-diglycerides and propylene glycol, said emulsifier being present in an amount of about 2 to about 10 weight percent of the total composition, said composition containing about zero to about 10 weight percent of the total composition additional excipient.

17. The pharmaceutical composition according to claim 16 wherein said pharmacologically active compound is ibuprofen.

18. The pharmaceutical composition according to claim 16 wherein said pharmacologically active compound is trimethoprim.

19. A process for preparing a controlled release oil-in-water emulsion pharmaceutical composition, said emulsion being stable at a pH value of about 5.5 to about 7.5 but separating at a pH value of less than about 2.0 into water and oil phases that comprises the steps of:

(a) providing a homogeneous molten admixture at a temperature below about 85° C., said molten admixture containing (i) wax matrix having dissolved or dispersed therein (ii) a pharmaceutically effective amount of a pharmacologically active compound and (iii) a phospholipid emulsifier, said matrix being a wax having a melting point of about 40° C. to about 80° C., said pharmacologically active compound being free from decomposition below about 90° C., the ratio of said wax matrix to said emulsifier being about 1:1 to about 5:1;

(b) providing an aqueous phase at a temperature about 5° C. higher than that of said molten admixture;

(c) microemulsifying said molten admixture as oil phase with a sufficient amount of said aqueous phase at the temperature of said aqueous phase is external, in which the average oil phase particle size is about 100 nm to about 250 nm, and in which the relative amounts of aqueous and oil phases are within about 20 percent of the final percentages desired for those phases;

(d) cooling the resultant emulsion to a temperature of about 10° to about 40° C.; and (e) admixing zero to about 10 weight percent of the total composition additional excipient, sufficient water and adjusting the pH value such that the formed pharmaceutical composition has a viscosity at 20°–25° C. of about 1 to about 1000 cps, a pH value of about 4.5 to about 8.0, a water phase that constitutes at least 25 weight percent of the total composition, an oil phase that contains (i) the wax matrix constituting about 3 to about 30 weight percent of the total composition, (ii) the emulsifier constituting about 2 to about 20 weight percent of the total composition, and (iii) the pharmacologically active compound.

20. The process according to claim 19 wherein said homogeneous molten admixture is at a temperature of about 70° to about 80° C. when admixed with said water phase.

21. The process according to claim 20 wherein the wax of said wax matrix has a melting point of about 45° to about 70° C.

22. The process according to claim 19 wherein said emulsifier is a phospholipid.

23. The process according to claim 22 wherein said emulsifier is a vegetable lecithin admixed with ethoxylated mono-diglycerides and propylene glycol.

* * * * *